United States Patent [19]

Takemura et al.

[11] 4,398,540
[45] Aug. 16, 1983

[54] COMPOUND MODE ULTRASOUND DIAGNOSIS APPARATUS

[75] Inventors: Yasuhiko Takemura, Nishinasuno; Takahisa Okazaki, Otawara, both of Japan

[73] Assignee: Tokyo Shibaura Denki Kabushiki Kaisha, Kawasaki, Japan

[21] Appl. No.: 204,003

[22] Filed: Nov. 4, 1980

[30] Foreign Application Priority Data

Nov. 5, 1979 [JP] Japan .................. 54-143095
Nov. 9, 1979 [JP] Japan .................. 54-145150

[51] Int. Cl.³ ........................................... A61B 10/00
[52] U.S. Cl. .................................. 128/660; 128/661; 358/1.2
[58] Field of Search ............... 128/660-661,663; 358/112; 73/625-626, 861.25

[56] References Cited

U.S. PATENT DOCUMENTS

| | | | |
|---|---|---|---|
| 4,058,001 | 11/1977 | Waxman | 128/660 |
| 4,135,139 | 1/1979 | Buchner | 128/660 |
| 4,240,295 | 12/1980 | Uranishi | 128/660 |
| 4,257,278 | 3/1981 | Papadofranjakis et al. | 128/663 |
| 4,318,413 | 3/1982 | Iinuma et al. | 128/660 |

OTHER PUBLICATIONS

Yokoi et al., "Real-Time UTS Diagnostic System", Electronic Engineering in Japan No. 132, Dec. 1977, pp. 20-26.
Sato et al., "Electronic Sector Scanning", Toshiba Review, No. 119, Jan-Feb. 1979, pp. 20-24.

*Primary Examiner*—Kyle L. Howell
*Assistant Examiner*—Francis J. Jaworski
*Attorney, Agent, or Firm*—Finnegan, Henderson, Farabow, Garrett & Dunner

[57] ABSTRACT

B-mode image data obtained by using an electronic linear scanning probe are loaded into a first memory area of a frame memory in a memory format corresponding to a B-mode ultrasound beam. An ultrasound echo signal corresponding to a given location on the B-mode image is sampled so as to derive M-mode image data which are in turn loaded into a second memory area of the frame memory. The B-mode image data and the M-mode data, so stored, are simultaneously read out in a television format from the frame memory, so that the B-mode image and the M-mode image are concurrently displayed on the screen of a television monitor side by side. The M-mode image data may be substituted with Doppler data in order to concurrently display the B-mode image and the Doppler data (frequency spectrum) on the screen of the television monitor.

10 Claims, 27 Drawing Figures

FIG. 7A CONTROL PULSE

FIG. 7B B-MODE RATE PULSE

FIG. 7C M-MODE RATE PULSE

FIG. 13A  CONTROL PULSE
FIG. 13B  B-MODE ENABLE SIGNAL
FIG. 13C  RASTER ADDRESS DATA
FIG. 13D  B-MODE ULTRASOUND IMAGE SIGNAL

FIG. 14A  CONTROL PULSE
FIG. 14B  DOPPLER MODE ENABLE SIGNAL
FIG. 14C  RANGE GATE SIGNAL
FIG. 14D  SAMPLE-HOLD SIGNAL
FIG. 14E  FREQUENCY SPECTRUM SIGNAL

COMPOUND MODE ULTRASOUND DIAGNOSIS APPARATUS

BACKGROUND OF THE INVENTION

The present invention relates to a compound mode ultrasound diagnosis apparatus capable of concurrently displaying at least two different kinds of ultrasound images or data on a single TV monitor screen.

In diagnosing a heart of an unborn child, for example, by means of the ultrasound diagnosis apparatus, commonly used is a method in which a B-mode image on real time is displayed on a display screen by using a high speed electronic scanning system while at the same time data on a desired location or locations in the B-mode image are sampled so that an M-mode image is displayed on another separate display screen. For displaying the B-mode image, an X-Y monitor of the short storage type, is employed, since the image formed through a high speed electronic scanning must be displayed on the real time basis. For the M-mode image, an X-Y monitor of the storage type is used since the image formation is made at relatively low speed.

A correlation between an instantaneous motion of the whole heart and a motion of a particular portion of the heart is very useful for the heart diagnosis of an unborn child. It is for this reason that the concurrent display of the B-mode image on the real time basis and the M-mode image is employed. For ease of grasping the correlation between the B- and M-mode images, photographing simultaneously both the images, and recording the images by a video tape recorder, it is desirable that both images be concurrently displayed side by side on the same screen, not on separate screens.

To meet the desire of the concurrent display of both the images has been considered difficult in that there is a difference between the characteristics of the two images or data required for the display, and that a complicated scanning operation is necessary for realizing the concurrent display of the different images on a single screen.

SUMMARY OF THE INVENTION

Accordingly, an object of the present invention is to provide a compound mode ultrasound diagnosis monitor apparatus capable of concurrently displaying at least two kinds of ultrasound images or data on a screen of a monitor display in a simple manner.

According to one aspect of this invention, there is provided a compound mode ultrasound diagnosis apparatus comprising:

a phased array transducer for radiating at least two kinds of ultrasound beams toward an object under examination and for receiving ultrasound echo echoes reflected therefrom;

a circuit arrangement for processing the ultrasound echo so as to obtain two kinds of ultrasound echo signals;

a digital scan converter for converting the echo signals into television video signals; and a television monitor for displaying the television video signals;

the digital scan converter including an analog-to-digital converter for converting the ultrasound echo signals into two kinds of digital ultrasound echo data, a frame memory for storing the two kinds of digital ultrasound echo data, a write control circuit for respectively writing the two kinds of digital ultrasound data into first and second memory areas of the frame memory, a read control circuit for reading out the two kinds of digital ultrasound data in accordance with a television format, and a digital-to-analog converter for converting the digital ultrasound data read out from the frame memory into television video signals.

DETAILED DESCRIPTION OF THE PREFERRED EMBODIMENTS

Figure 1:
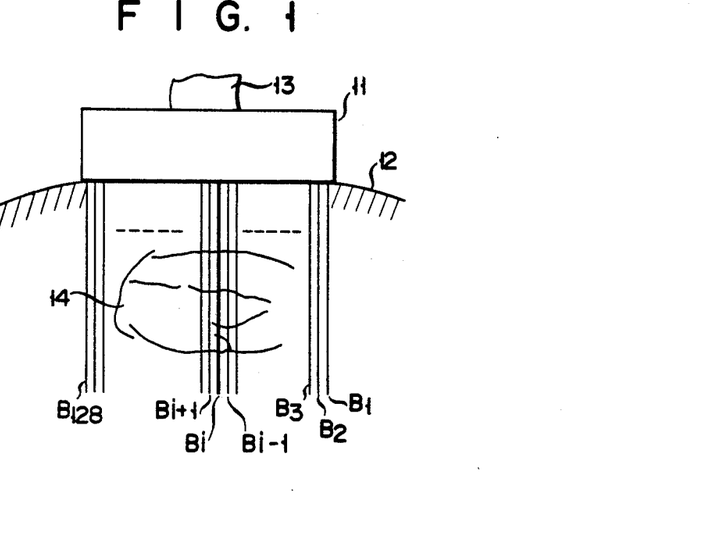
FIG. 1 illustrates a scanning method to take a B-mode (tomogram) image and an M-mode image of a human body by using an electronic linear scan type ultrasound probe.

In a scanning method used in an embodiment of the compound mode ultrasound diagnosis apparatus according to the invention, schematically illustrated in FIG. 1, an electronic scanning probe 11 is used in contact with the surface of a human body 12 at the time of diagnosis. The electronic scanning probe 11, composed of a phased array ultrasound transducer, is coupled with a main unit of the dual mode ultrasound diagnosis apparatus, through a line 13. The present embodiment is so constructed as to concurrently display on a single TV monitor screen a B-mode real time tomogram of a heart 14 in the human body 12 formed by using the electronic scanning probe 11 and M-mode image data formed by sampling an ultrasound echo. The M-mode image is known as a sampling ultrasound cardiogram (briefly called a sampling U.C.G. or a simultaneous U.C.G.).

In FIG. 1, driving electric pulse signals delivered through the line 13 from the main unit of the ultrasound diagnosis apparatus (not shown) are supplied to the ultrasound transducers within the probe 11 in a given order. The probe 11 sequentially radiates toward the heart 14, 128 ultrasound beams $B_1$, $B_2$, ... $B_{i-1}$, $B_i$, $B_{i+1}$, ... $B_{127}$, $B_{128}$, for example. Every time each of the respective beams $B_i$ (i=1, 2, 3, ... 128) is radiated, the probe 11 is switched from a radiation mode to a receiving mode. Under this condition, ultrasound echoes reflected from the inside of the human body 12 are converted, by the ultrasound transducers in the probe 11, into echo signals which in turn are sent through the line 13 to the main unit of the ultrasound diagnosis apparatus. The echo signals are properly processed in the main unit to be transformed into echo data which are then stored in a frame memory 15 shown in FIG. 2.

Figure 2:
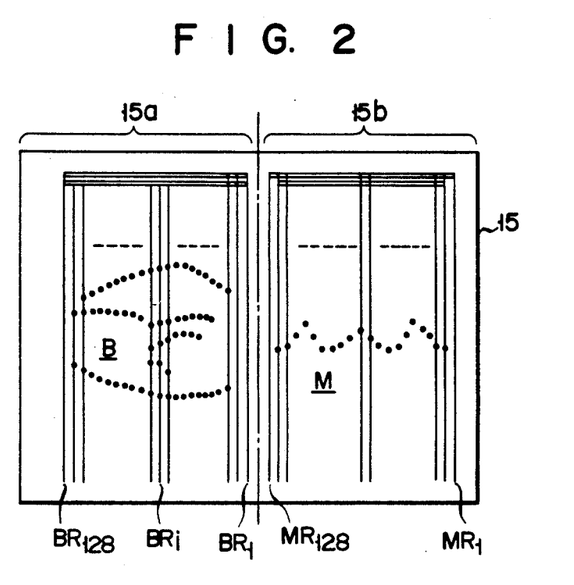
FIG. 2 is a memory format illustrating a state that the data obtained by the scanning method shown in FIG. 1 are stored in a frame memory.

The frame memory 15 having a memory capacity of one frame of the TV monitor screen includes a first memory area 15a corresponding to the left half of the screen of the monitor and a second memory area 15b corresponding to the right half of the screen. Assuming now that the one frame of the TV monitor is formed of $256 \times 512 \times 4$ bits. RAM (random access memory) composed of an MOS memory or a bipolar memory may be used as the frme memory. The first memory area 15a stores the data of the B-mode real time tomogram. The second memory area 15b stores the data of the M-mode image. The first memory area 15a has 128 X addresses, $BR_1$, $BR_2$, ... $BR_i$, ... $BR_{128}$. The number of the memory address locations is the same as that of the beams $B_1$, ... $B_i$, ... $B_{128}$. The number of the Y-address locations is 512. The X-, Y-addresses are designated by outputs of a frame memory address generator. The echo data, obtained through one scanning by a sequence of the beams $B_1$ to $B_{128}$, are written in turn into the memory locations $BR_1$, $BR_2$, ... $BR_{128}$ by the X-addresses. At each of the memory locations $BR_1$ to $BR_{128}$ the data are written into the first memory area 15a from the upper end to the lower end thereof in the figure by the Y-addresses. In the B-mode real time scanning, the repetition rate of the ultrasound beam scanning is several tens per second, at least ten and several repetitions per second in order to obtain effective diagnostic information. The data stored in the memory area 15a in the frame memory 15 are updated substantially on a real time basis.

Meanwhile, the M-mode data can be obtained by using the sampling U.C.G. method which will be described in detail hereinafter. The M-mode data are formed by sampling an ultrasound echo at a predetermined position every time 8 ultrasound beams, for example, are radiated. This will be described by referring to FIG. 1 in which after 7 ultrasound beams $B_1$, $B_2$, ... $B_7$ are each sequentially radiated an ultrasound beam $B_i$ is radiated at the predetermined position. Then, 7 ultrasound beams $B_8$, $B_9$, ... $B_{14}$ are each sequentially radiated and the ultrasound beam $B_i$ is again radiated at the predetermined position. In this manner, many sets of 8 ultrasound beams are radiated in turn and ultrasound echo signals of the ultrasound beams $B_i$ are processed to obtain M (U.C.G.)-mode image data. The M-mode image data thus obtained are written into the right half memory area 15b of the frame memory 15 in the similar manner as the B-mode image data in which the M-mode image data are written into the memory locations $MR_1$, $MR_2$, ... $MR_{128}$ in the order under the designation of the X-addresses and at each of the locations $MR_1$ to $MR_{128}$ the M-mode data are written from the upper portion to the lower portion thereof under the designation of the Y-addresses.

The B-mode image data and the M-mode image data, which are stored in the frame memory 15, are all together converted into a television format (a standard system of the television scanning), for example, and then are simultaneously displayed on a single screen of the monitor display, side by side. For this reason, the B-mode image and the M-mode image on the monitor screen substantially correspond to the memory format shown in FIG. 2. To display the data stored in the frame memory 15 on the monitor screen, a digital scan converter is used, which will be described in detail hereinbelow.

Figure 3:
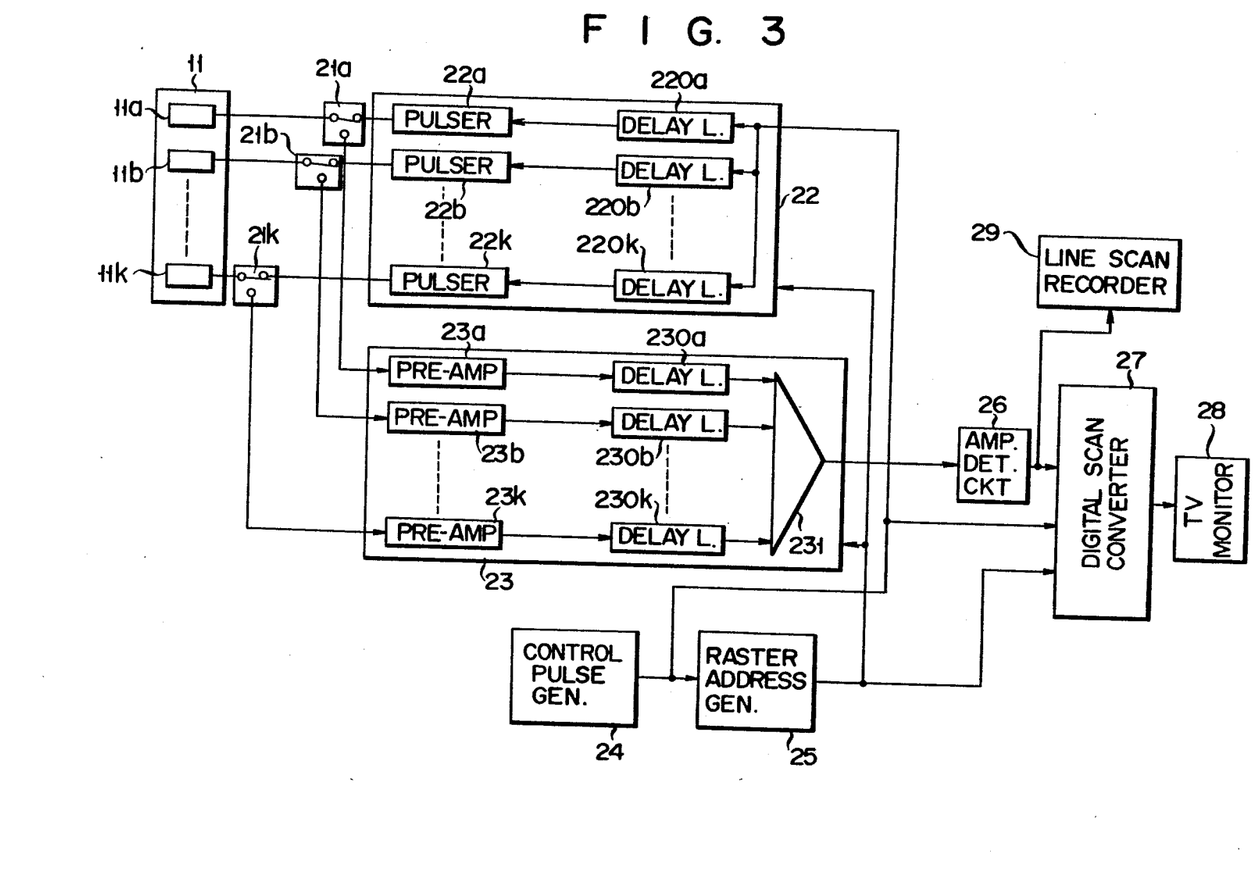
FIG. 3 is a block diagram of a circuit arrangement of an embodiment of an ultrasound diagnosis apparatus according to the invention.

The arrangement of the embodiment of the ultrasound diagnostic apparatus of the invention will be described by referring to FIGS. 3 and 4. As shown in FIG. 3, the probe 11 shown in FIG. 1 is an array of ultrasound transducers 11a, 11b, ... 11k, (k being an integer), which are disposed closely to one another in practical use, in order to improve a resolution of the images formed. The ultrasound transducers 11a, ... 11k, respectively, are connected to pulsers 22a, 22b, ... 22k, (k being an integer), in a pulser unit 22 or preamplifiers 23a, 23b, ... 23k in a receiving unit 23, by way of switches 21a, 21b, ... 21k for switching between transmission and reception. In the transmission mode, the switches 21a to 21k are so switched as to transmit electric pulses from the pulsers 22a to 22k to the transducers 11a to 11k. In the receiving mode, those switches 21a to 21k are switched so that the echo signals derived from the transducers 11a to 11k are supplied to the preamplifiers 23a to 23k.

The pulser unit 22 is comprised of pulsers 22a to 22k and a plurality of delay lines 220a, 220b, ... 220k, (k being an integer), connected to the input sides of the pulsers 22a to 22k. Control pulses generated from a control pulse generator 24 are commonly supplied to the inputs of the delay lines 220a to 220k. The control pulses supplied to the delay lines 220a to 220k, respectively, are delayed by given time intervals and supplied as driving pulses to the pulsers 22a to 22k. In response to the driving pulses, the pulsers 22a to 22k generate transducer driving pulses. The pulser unit 22 is controlled by a raster address signal delivered from a raster address generator 25 driven by the control pulse generated from the control pulse generator 24, so that the control pulse is supplied to the delay lines 220a to 220k so as to effect given beam scanning and beam focusing. The method to scan and focus the ultrasound beams by using the raster address signal is well known, and no further explanation will be given here.

The receiving unit 23 is comprised of preamplifiers 23a to 23k, (k being an integer), for amplifying the echo signals delivered from the transducers 11a to 11k through the switches 21a to 21k, delay lines 230a, 230b, ... 230k, (k being an integer), to delay by given time period the echo signals amplified by the preamplifiers 23a to 23k, and an adder 231 for summing the output signals from the delay lines 230a to 230k. The receiving unit 23 is also supplied with the raster address signal from the raster address generator 25, as in the case of the pulser unit 22. With the raster address signal received, the focusing and summing of the echo beams are performed corresponding to the beam scannings in the transmission mode. The scanning and focusing of the echo beams by using the raster address signal are easily performed by a well known ultrasound signal processing method, and no detailed description thereof will be given here.

The summed or synthesized echo signal derived from an output terminal of the adder 231 is amplified and detected by an amplifier/detector circuit 26 of which the output is supplied to one of the input terminals of a digital scan converter 27. The digital scan converter 27, containing the frame memory 15 shown in FIG. 2, converts the summed echo signal into a television format signal. The television format signal converted is supplied to a television monitor 28 where it is visualized. The conversion of the summed echo signal into the television format signal is performed under control of the control pulse and the raster address signal applied from the generators 24 and 25 to the digital scan converter 27. A line scan recorder 29 may be connected to the output of the amplifier/detector circuit 26.

An example of the digital scan converter 27 will be described by referring to FIG. 4. The summed echo signal outputted from the amplifier/detector circuit 26 in FIG. 3 is converted into digital ultrasound echo data in an analog-to-digital (A/D) converter 27a. The digital ultrasound echo data corresponding to one ultrasound beam, for example, the beam $B_1$ in FIG. 1, is stored in an input line buffer memory 27b. The digital ultrasound echo data for one ultrasound beam temporarily stored in the line buffer memory 27b are sequentially loaded into the memory locations of the frame memory 15 in address sequence under control of the timing signal supplied from the timing signal generator 27c. As a matter of course, the A/D converter 27a and the line buffer memory 27b also operate under control of the timing signal generator 27c. The timing signal generator 27c generates signals of given timing, in accordance with the control pulse from the control pulse generator 24 and the raster address signal from the raster address generator 25 shown in FIG. 3.

While the B-mode image data are loaded into the first memory area 15a, an M-mode ultrasound echo signal of the beam $B_i$ in FIG. 1 is sampled and the sampled (M-mode image) data are sequentially stored into the memory area 15b of the frame memory 15. The data stored in the frame memory 15 are read out in accordance with the television format. The data are loaded to an output line buffer memory 27d and the data read out therefrom are in turn supplied to a digital-to-analog (D/A) converter 27e. The D/A converter 27e converts the data into an analog signal and applies the obtained analog signal as a video signal to the TV monitor 28.

Figure 4:
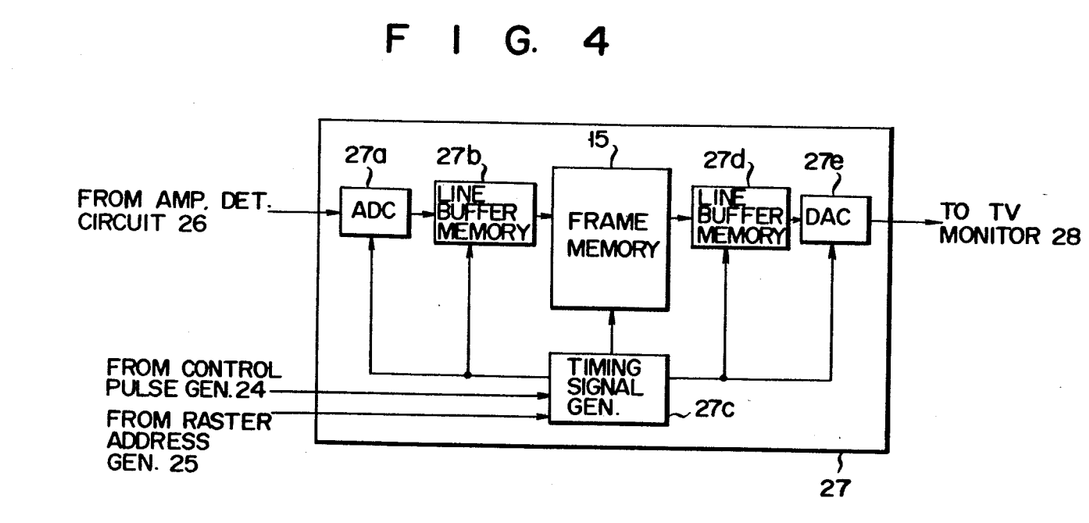
FIG. 4 is a block diagram of a digital scan converter used in the circuit arrangement shown in FIG. 3.
Figure 5:
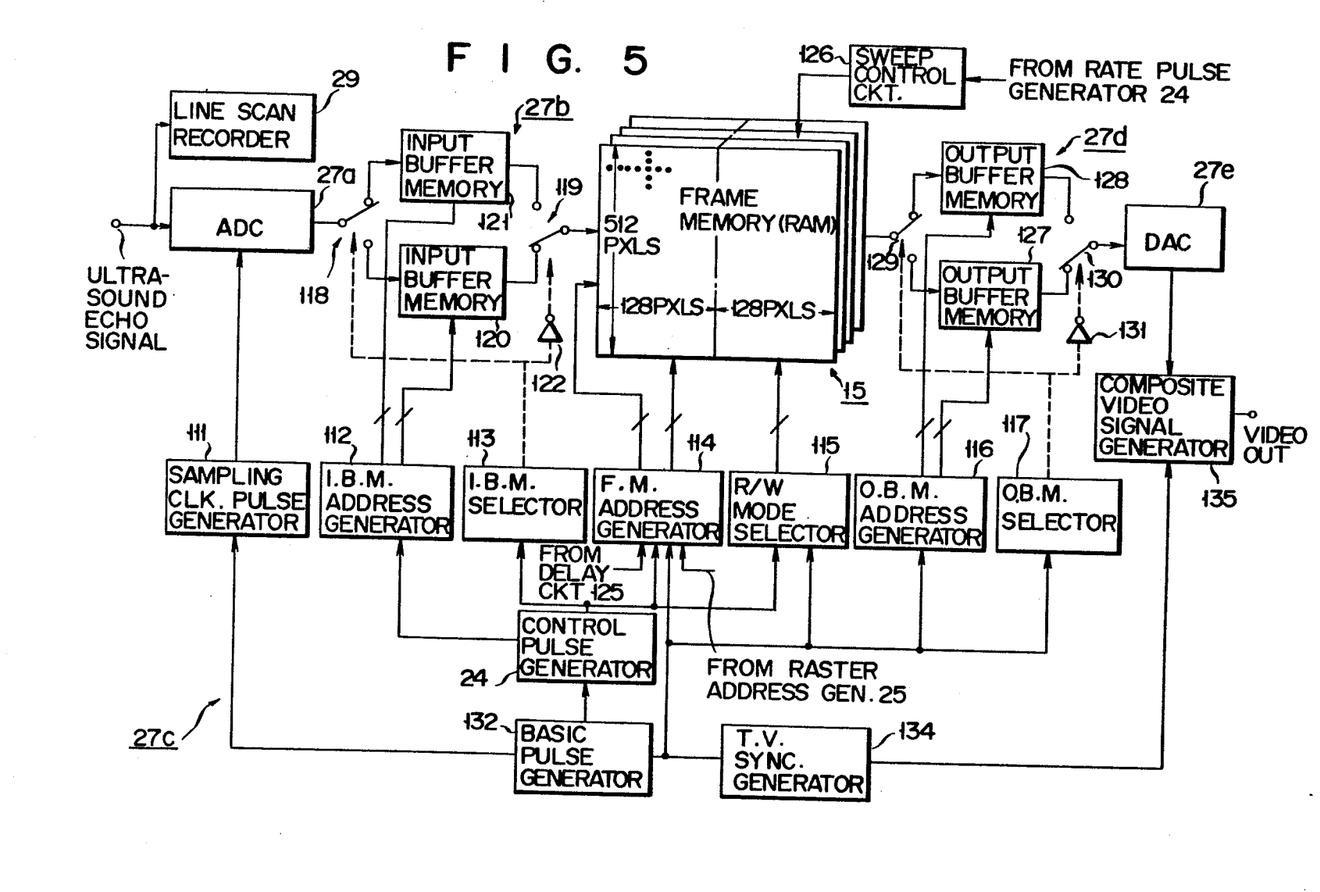
FIG. 5 is a detailed block diagram of a circuit arrangement of the digital scan converter shown in FIG. 4 and the associated circuits thereof.

Turning now to FIG. 5, there is shown in block form the detail of the digital scan converter shown in FIG. 4 and the associated circuit thereof. As shown, the timing signal generator 27c is comprised of a rate pulse generator 24, a sampling clock pulse generator 111, an input buffer memory address generator 112, an input buffer memory selector 113, a frame memory address generator 114, a read/write mode selector 115, an output buffer memory address generator 116, an output buffer memory selector 117 and a basic pulse generator 132. The timing signal generator 27c becomes operative in synchronism with the basic pulse from the basic pulse generator 132. The ultrasound echo signals are converted into digital ultrasound data in the A/D converter 27a which have 4 bits per pixel in accordance with the sampling clock pulse generated from the sampling clock pulse generator 111. The ultrasound image data are supplied through a switching circuit 118 to the line buffer memory 27b where the data are temporarily stored.

The line buffer memory 27b is comprised of two input buffer memories 120 and 121, each of which has a memory capacity of $512 \times 4$ bits and stores the ultrasound image data obtained from an ultrasound echo signal. The input buffer memories 120 and 121 are switched to be alternately in the write mode and the read mode under control of the switching circuits 118 and 119 which are alternately switched by the output signal from the input buffer memory selector 113. An inverter 122 inverts the output signal of the input buffer memory selector 113 which in turn is applied to the switching circuit 119. In a state of the line buffer memory 27b as illustrated, the input buffer memory 121 is in the write mode and stores the ultrasound image data of the ultrasound beam $B_i$ while the input buffer memory 120 is in the read mode and provides the ultrasound image data of the ultrasound beam $B_{i-1}$ to the frame memory 15. The read/write address of these input buffer memories 120 and 121 are supplied from the input buffer memory address generator 112. In the frame memory 15, the B-mode image data and the M-mode image data are both written thereinto in the same direction as that of the scan of each ultrasound beam in accordance with an X-address and a Y-address, which are supplied from the frame memory address generator 114.

Assume now that the maximum diagnostic depth is 18 cm, the propagating speed of the ultrasound in the human body is 150,000 cm/sec, and the rate blanking period is 40 $\mu$sec. On this assumption, the period of the ultrasound beam radiation, i.e., the repetitive period of the rate pulse, is 274 $\mu$sec (=40 $\mu$sec+13 $\mu$sec/cm $\times$ 18 cm). Here, 13 $\mu$sec is the propagating time of the ultrasound in the ultrasound diagnostic depth of 1 cm. When the ultrasound reflection is considered, the ultrasound propagates 2 cm and hence 2 cm/$15 \times 10^4$ cm/sec $\approx$ 13 $\mu$sec.

Figure 6A:
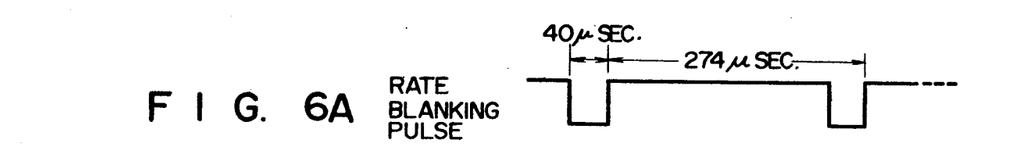
FIGS. 6A to 6D and FIGS. 7A to 7C show timing charts useful for explaining the operation of the circuit of FIG. 5.
Figures 6B, 6C, 6D:
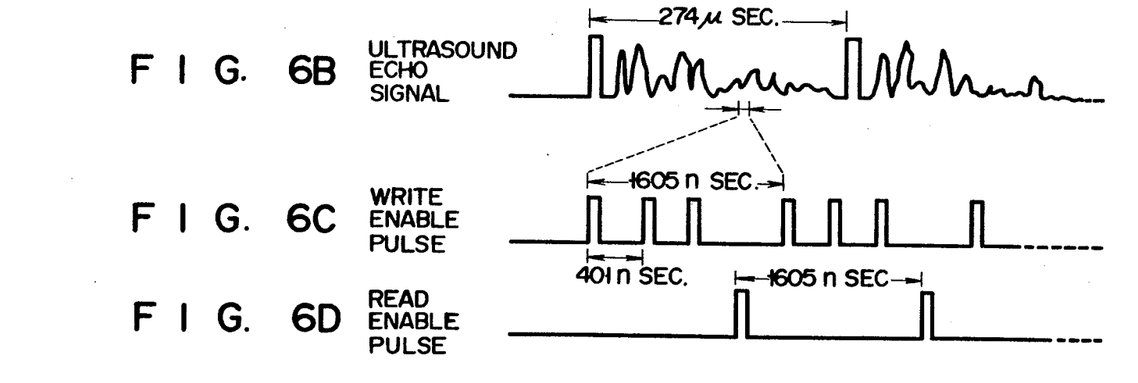

The rate blanking pulse and the ultrasound echo signal take waveforms as shown in FIGS. 6A and 6B, respectively. During the repetitive period of the control pulse, the data in one column of the frame memory, i.e., the data of 512 pixels, must be written into the frame memory 15. Since the memory cycle time of the frame memory 15 is very short, the stored image data can be read out approximately one time during a period that the data of 3 pixels are written into the frame memory. Since the data of 512 pixels of one column of the frame memory may be loaded within 274 $\mu$sec, the data of 3 pixels may be loaded within 1,605 nsec. Accordingly, the read/write mode selector 115 produces three write enable pulses and one read enable pulse during the period of 1,605 nsec, as shown in FIGS. 6C and 6D. The read enable pulse has a repetitive period of 1,605 nsec.

In order to display the image data on the TV monitor, within 63.5 $\mu$sec which is equal to the period of the one horizontal synchronizing pulse, the image data of 256 pixels must be read out from the frame memory 15 and must be stored into the output buffer memory 27d. There are 256 pixels in a television raster direction (an X-axis direction of the frame memory 15) orthogonal to the scan direction for the image data writing. Accordingly, 248 nsec is required for 1 pixel, so that the image data of 8 pixels in the television raster direction are simultaneously read out from the frame memory 15 to be transferred to the output buffer memory 27d. The address of the frame memory 15 is designated by the output pulse of the frame memory address generator 114, and a read/write enable pulse is produced by a read/write mode selector 115.

Figures 7A, 7B:
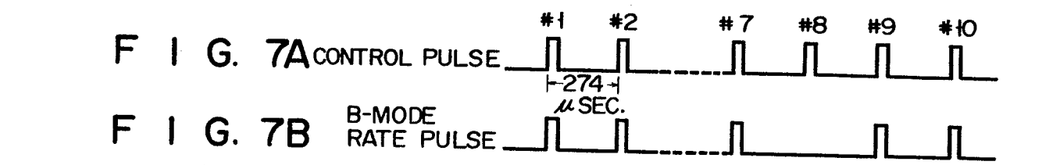
Figure 7C:
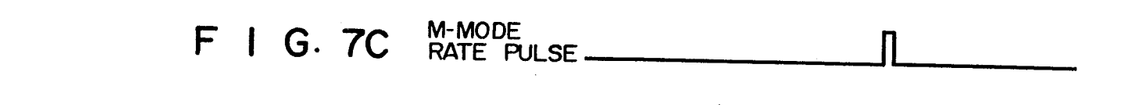

In connection with the address of the frame memory 15, the sampling U.C.G. for obtaining the M-mode image signal will be described in detail. As previously stated, the sampling U.C.G. may be obtained from the ultrasound echo signal at the location of the ultrasound beam $B_i$ (indicated by a thick line in FIG. 1), for example, every time the control pulse generator 24 produces 8 control pulses. The control pulse is generated from the control pulse generator 24 every 274 μsec, as shown in FIG. 7A. Since 7 out of every 8 control pulses of the control pulse train are used for the B-mode control pulses and the remaining one control pulse for the M-mode control pulse, the ultrasound beam steering control may be made such that the scan is made of the ultrasound beams $B_1, B_2, \ldots, B_7$ and the ultrasound beam $B_i$ is produced, and then the scan is made of the succeeding ultrasound beams $B_8, B_9, \ldots, B_{14}$ and the ultrasound beam $B_i$ is again produced.

Figure 8:
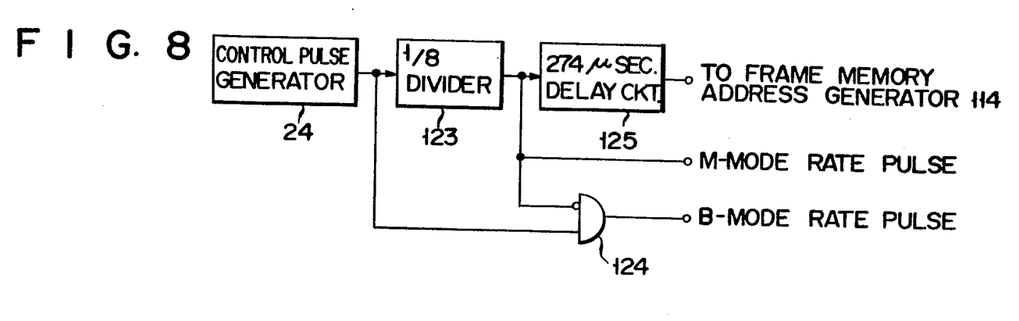
FIG. 8 shows a block diagram of an ultrasound beam steering control circuit.

FIG. 8 is an ultrasound beam steering control circuit arrangement. In the circuit arrangement, the control pulse train from the control pulse generator 24 is divided by a ⅛ divider 123, thereby to produce the M-mode control pulse. The M-mode control pulse is in turn applied to the inhibit input terminal of an AND gate 124 while the control pulse is applied to the other input terminal of the AND gate 124. As a result, the B-mode control pulses are produced. Such a circuit arrangement that the ultrasound beams $B_1, B_2, \ldots, B_7$ are radiated in accordance with the B-mode control pulses and the ultrasound beam $B_i$ at a given location is radiated in accordance with the M-mode control pulses, is well known and therefore the explanation of the circuit arrangement will be omitted. The M-mode control pulse outputted from the ⅛ divider 123 is delayed by 274 μsec in a delay circuit 125 and then is applied to a frame memory address generator 114. It is for this reason that since the ultrasound image data read out from the input buffer memory 27b is that formed by the ultrasound beam before one rate pulse, the M-mode image data must be written into the memory area 15b of the frame memory 15 after it is delayed by approximately 274 μsec of one control pulse period.

The output signal of the raster address generator 25 (FIG. 3) is supplied to the frame memory address generator 114 to know which ultrasound beam is radiated mainly in order to obtain the ultrasound image data of the B-mode. A sweep control circuit 126 is provided to supply an M-mode sweep control signal to the frame memory 15 which is in synchronism with the rate pulse.

Generally, the M-mode image is used to observe a motion of the valve in the heart with respect to time which is relatively of a slow speed. Accordingly, it is desirable to observe the motion of the valve over 1 second or 2 seconds, for example. In the sampling U.C.G., the time taken for the M-mode image to be written into the memory area 15b is 281.6 msec (=8 control pulses/sec×275 μsec×128 pixels). Therefore, when the sweep time of 1 μsec is set up by an operator, it is necessary to write the M-mode image in the memory area 15b every approximately 4 M-mode ultrasound beams under control of the output from the sweep control circuit 126. Since the M-mode data may be read out from the frame memory 15 in accordance with the manner previously described, the CRT display allows the M-mode image with the sweep time of one second to be displayed, so that the operator simultaneously observes the B-mode image in connection with the M-mode image for diagnosis. For further detailed data, a hard copy is available by the line scan recorder 29 which records the ultrasound echo signals including the M-mode echo signals as they are.

The output line memory 27d has output buffer memories 127 and 128 each for storing the video data of one horizontal synchronism pulse period of the TV monitor 28. The output video data of the frame memory 15 are alternately written into the output buffer memories 127 and 128, through a switching circuit 129. The video data stored are alternately read out from the output buffer memories 127 and 128 into a digital-to-analog converter 27e, through a switching circuit 130. The switching circuits 129 and 130 are controlled by the output buffer memory selector 117. Incidentally, the output signal of the output buffer memory selector 117 is inverted by an inverter 131 and supplied to the switching circuit 130. The addresses of the output buffer memories 127 and 128 are designated by the output buffer memory address generator 116. Note here that the address designation must be made such that in the write mode the data of 8 pixels are simultaneously written while in the read mode the data are sequentially read out for each pixel and supplied to the digital-to-analog (D/A) converter 27e where in turn the digital data are converted into analog video signals. The switching circuits 129 and 130 are switched every one horizontal synchronizing period 63.5 μsec and the output buffer memories are switched at the period to alternately be in the read and write modes. The output pulse of the control pulse generator 132 is also supplied to a TV synchronizing pulse generator 134 where the horizontal synchronizing pulse and the vertical synchronizing pulse are generated. The analog video signals of the D/A converter 27e and the output of the TV synchronizing pulse generator 134 are synthesized in a composite video signal generator 135 to produce a TV video signal, which is provided to the TV monitor 28. It will be seen that upon designation of the address of the frame memory address generator 114, the ultrasound image may be displayed by the TV monitor 28 both in the interlace raster scan and in the non-interlace raster scan modes.

In this way, the present embodiment simultaneously displays the M-mode image and the B-mode image on the screen of the television monitor. Therefore, the comparison of both the images is easy and the correct diagnosis is ensured. Particularly, for the diagnosis by using a photograph taken of the ultrasound images, the ultrasound diagnosis apparatus of the embodiment is very effective, since the photograph has the B-mode image and the M-mode image, which are taken at the same timing.

Although not referred to in the above description, the M-mode marker representing a location for collecting the M-mode image data may be used in the B-mode image, as in the case of this type of the device capable of doing the sampling U.C.G. display.

As described above, the B-mode image and the M-mode image obtained by using the same electronic linear scanning probe are stored into the memory areas 15a and 15b of the frame memory 15. Those are together read out and are displayed side by side on the single TV screen. The other methods available for obtaining the B-mode image data are an electronic sector scan, a mechanical high speed scan, and a contact compound mechanical scan. In addition, an independent single probe for obtaining M-mode image data may be placed at a desired position for sampling U.C.G.

Images other than the M-mode image and the B-mode image may be stored in the frame memory and displayed side by side on the TV monitor screen.

Alternatively, the B-mode image data previously obtained is prestored in the first memory area while the image data formed on the real time basis is stored into the second memory area. The image data thus stored are used for the concurrent display. As a matter of course, the memory capacity of the frame memory is not limited to that of one frame but may be more than that.

Figure 9:
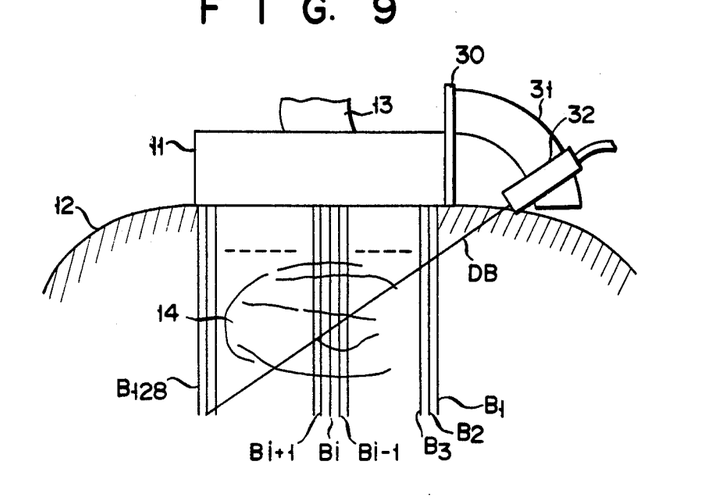
FIG. 9 illustrates a method to take a B-mode (tomogram) ultrasound echo and Doppler ultrasound echo according to another embodiment of the present invention.

Turning now to FIG. 9, there is shown diagrammatically another embodiment of a compound mode ultrasound diagnosis apparatus to obtain the B-mode image by an electronic scanning probe 11 and a Doppler ultrasound echo by a single probe 32. In the description to follow, like reference numerals are used to designate like or substantially equivalent portions in FIGS. 1 to 8. The ultrasound Doppler data are useful for measuring velocity of a flow of blood. In diagnosing a heart, it is effective to observe the B-mode image or the M-mode image together with Doppler data. It is evident, in this case, that the Doppler data are preferably concurrently displayed, together with the B-mode image or the M-mode image, on the same screen.

In FIG. 9, the B-mode tomogram of the heart 14 of an unborn child is formed by using the electronic linear scanning probe 11, as previously stated. The B-mode tomogram data are stored on the real time basis in the memory locations $BR_1$, $BR_2$, ..., $BR_{128}$ of the memory area 15a of the frame memory 15 shown in FIG. 10. The memory locations $BR_1$ to $BR_{128}$ are assigned with addresses corresponding to the ultrasound beams $B_1$, $B_2$, ..., $B_{128}$.

Figure 10:
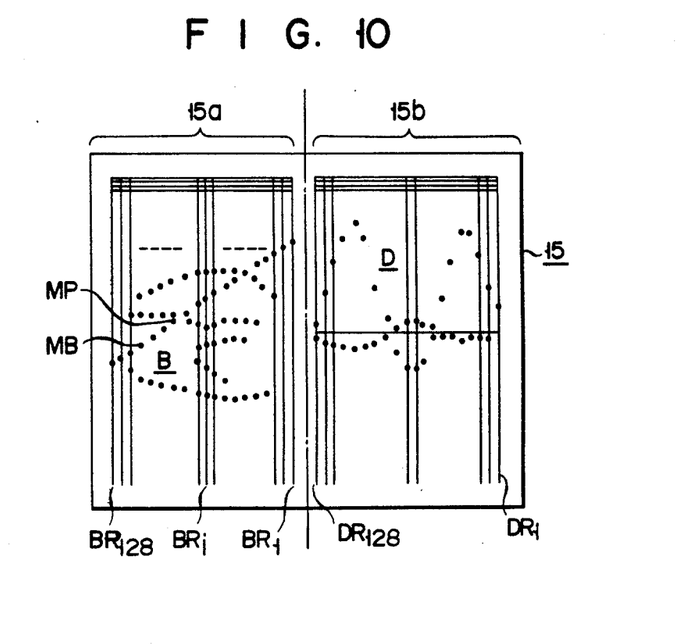
FIG. 10 is a memory format illustrating a state of the data obtained by the method shown in FIG. 9.

The Doppler data are stored on the real time basis at the locations $DR_1$, $DR_2$, ..., $DR_{128}$ of the memory area 15b of the frame memory 15. The locations $DR_1$ to $DR_{128}$ are assigned with addresses corresponding to the ultrasound beams which are projected for obtaining the Doppler data. Where, the frame memory 15 may be composed of a random access memory (RAM) with a memory capacity of $256 \times 512 \times 4$ bits like the first embodiment. The memory areas 15a and 15b have a memory capacity of $128 \times 512 \times 4$ bits, respectively.

On the side wall of the ultrasound probe 11 in FIG. 9, a side plate 30 is fixed to which one end of an arched supporting member 31 is fixed. A Doppler probe 32 is movably mounted on the supporting member 31 and movably along the surface of the supporting member 31. By moving the Doppler probe 32 along the supporting member 31, it is possible to adjust the location and direction of the ultrasound beam DB radiated from the probe 32 relative to the heart 14. The relative location and direction of the ultrasound beam DB may easily be found on the basis of the relative location of the probe 32 to the supporting member 31.

The compound mode display methods using the electronic linear scanning probe 11 and the Doppler probe 32 are:

(i) The method wherein the B-mode image and the Doppler data are alternately stored and displayed at short intervals of time. In the method, compound mode display can be realized substantially on the real time basis.

When ultrasound beams are alternately radiated from the electronic linear scanning probe 11 and the Doppler probe 32 every time one control pulse appears (the repetition pulse period of the control pulse being 274 $\mu$sec), the B-mode ultrasound echo and the Doppler echo are obtained therefrom. These echoes are processed in circuits hereinafter described so that the B-mode image data and the Doppler data are formed and these data are respectively stored in the memory areas 15a and 15b. At this time, as has been described in the first embodiment, while the data are written into the frame memory 15, the data can be read out of the frame memory 15 in the television format to display on the TV monitor 28 B-mode image and the Doppler information (frequency spectrum) on a real time basis.

(ii) The B-mode image data obtained by using the ultrasound probe 11 are stored in the memory area 15a of the frame memory 15 without renewing the stored data. At this time, only the Doppler data are updated in the memory area 15b. The B-mode image data are so read out exclusively as to be displayed freezingly while the Doppler information is displayed on a real time basis.

To this end, as described in the compound mode display method (i), the B-mode ultrasound image data and the Doppler data are first stored in the frame memory 15 on a real time basis. Then, the B-mode data stored in the memory area 15a are only read out without renewing the same, while the Doppler data stored in the memory area 15b are renewed and read out on the real time basis. Although, in the compound mode displaying method (ii), the B-mode ultrasound image data and the Doppler data are supplied alternately to the frame memory 15 on the real time basis, only the Doppler data are written into the memory area 15b. By reading out both the B-mode ultrasound image data and the Doppler data with the TV format, it will be understood that the Doppler data can be displayed on the real time basis while the B-mode ultrasound image is displayed in a freezing fashion. At this time, it is desirable to control the sweep time for the display of Doppler data as in the case of displaying the M-mode ultrasound image of the first embodiment because of the substantial nature of Doppler data.

The circuit arrangement of the compound mode ultrasound diagnosis apparatus according to the invention will be described by referring to FIG. 11. Like reference numerals are also used to designate like or equivalent portions in FIG. 3. The explanation about like or equivalent portions will be omitted and only the different portions will be described.

Figure 11:
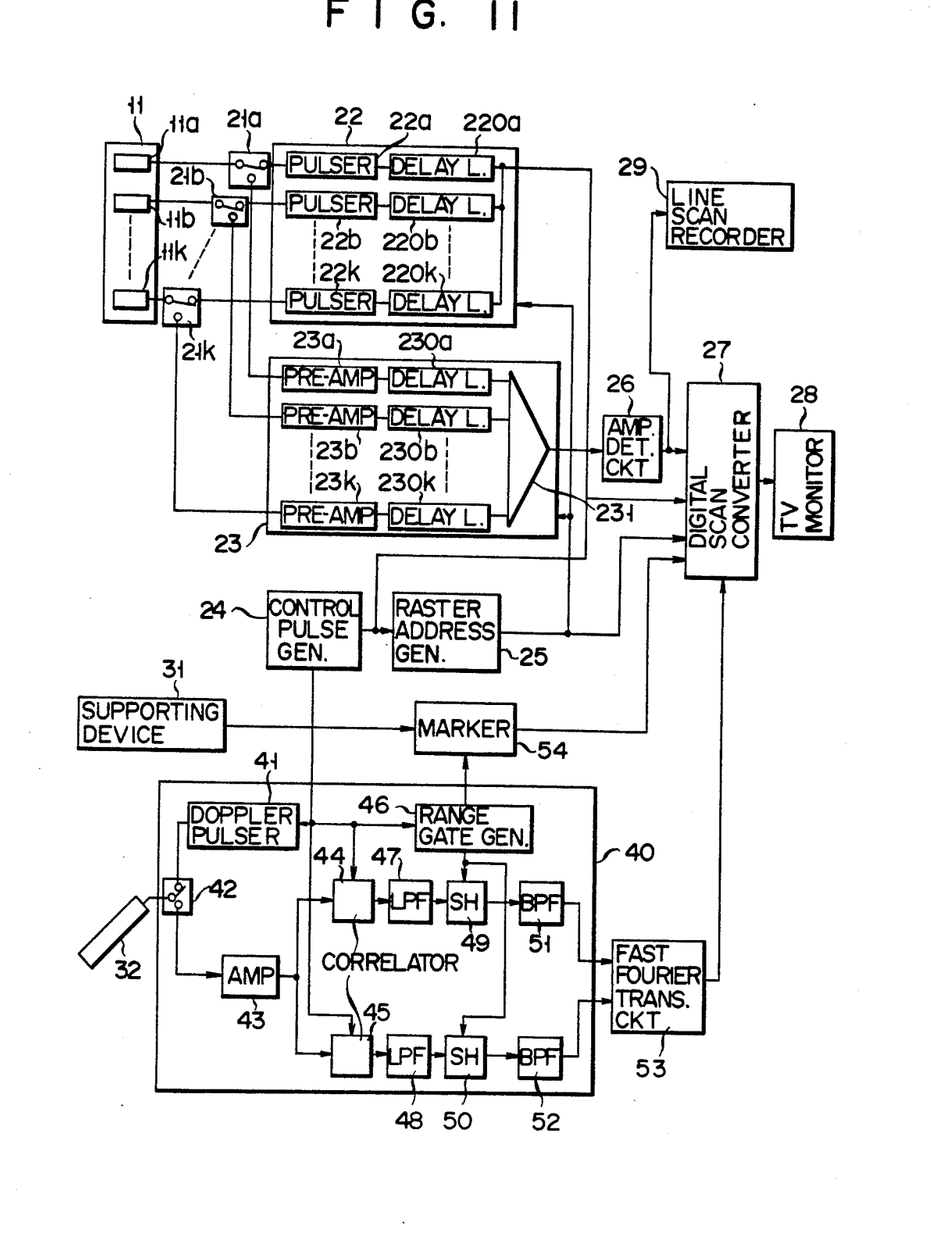
FIG. 11 is a block diagram of a circuit arrangement of another embodiment of the ultrasound diagnosis apparatus according to the present invention using the method shown in FIG. 9.

The Doppler probe 32 shown in FIG. 9 is driven when it receives the output pulse from a Doppler pulser 41 provided in a Doppler detector 40 in FIG. 11 by way of a switch 42. The ultrasound wave is emitted from the Doppler probe 32 toward the heart 14. The echo is received by the probe 32 where it is converted into an electrical Doppler echo signal. The Doppler echo signal is applied through the switch 42 to an amplifier 43 where it is amplified. The Doppler probe 32 and the electronic linear scanning probe 11 are driven alternately by the control pulse supplied from the control pulse generator 24. The control pulse is also applied to first and second correlation circuits 44 and 45 and a range gate generator 46, which are provided in the Doppler detector 40.

The Doppler echo signal outputted from the amplifier 43 is supplied to the first and second correlation circuits 44 and 45. The correlation circuits 44 and 45 are phase detecting circuits of which the outputs are applied to band-pass filters 51 and 52, through low-pass filters 47 and 48 and sample-hold circuits 49 and 50, respectively. A range gate signal from the range gate generator 46 is applied to the sample-hold circuits 49 and 50. The sampling timing of the gate signal is set up corresponding to the location where the Doppler deviation is detected. The Doppler deviation signals filtered out by the band-pass filters 51 and 52 are both supplied to a fast Fourier transform circuit 53. In the fast Fourier transform circuit 53, the Doppler deviation signal is transformed into a frequency spectrum signal which in turn is applied to the digital scan converter 27.

A signal representing the Doppler beam location MB detected by the supporting member 31 for supporting the Doppler probe 32 is sent forth to the marker circuit 54. A range gate signal representing the Doppler data sampling location on the Doppler beam DB is applied from the range gate generator 46 of the Doppler detector 40 to the marker circuit 54. The output signal of the marker circuit is applied to the digital scan converter 27, as a mark signal for indicating the beam direction mark MB and the location mark MP shown in FIG. 10.

The digital scan converter 27 includes the frame memory 15 having a data store format, as shown in FIG. 10. The digital scan converter 27 receives the rate pulse supplied from the rate pulse generator 24, the raster address signal from the raster address generator 25, the summed echo signal from the amplifier/detector circuit 26, the mark signal from the marker circuit 54, and the Doppler data signal from the fast Fourier transform circuit 53, respectively. In accordance with the raster address signal, the digital scan converter 27 writes the B-mode image data and the Doppler data into the frame memory 15 and reads out those into the monitor 28 in the television format. A detail of the digital scan converter is illustrated in FIG. 12.

Figure 15:
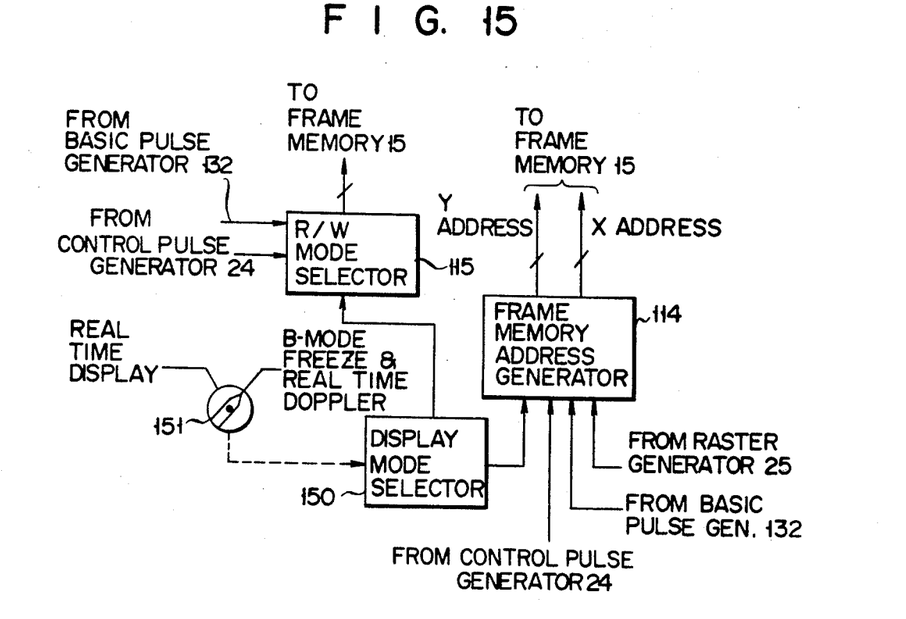
FIG. 15 shows a part of the circuitry of the digital scan converter of FIG. 12.

The digital scan converter 27 is substantially the same as that shown in FIG. 5 except that, since the Doppler data are handled therein for the M-mode ultrasound image data by the sampling U.C.G. method, different input signals are supplied to the frame memory address generator 114 and the read/write mode selector 115 in the timing signal generator 27c as will be described hereinafter by referring to FIG. 15.

Figure 12:
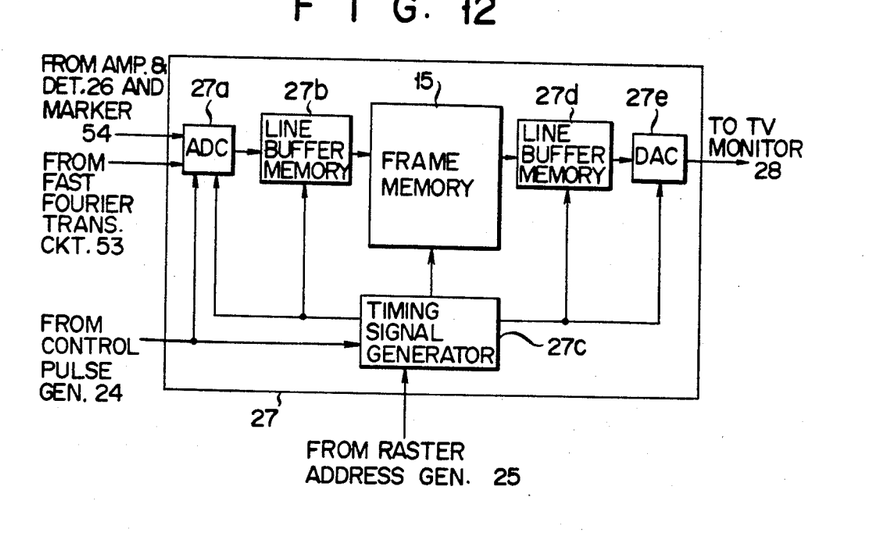
FIG. 12 is a block diagram of the digital scan converter used in the circuit shown in FIG. 11.

As shown in FIG. 12, the B-mode image data, marker signal and the Doppler data, which are analog signals, are supplied from the amplifier/detector circuit 26, marker circuit 54 and the fast Fourier transform circuit 53 to an A/D converter 27a where those are converted into digital signals. The digital signals (data of one rate pulse period) are stored in the line buffer 27b and the B-mode image data are loaded into the memory area 15a of the frame memory 15 in accordance with the data format shown in FIG. 10 while the Doppler data are written into the memory area 15b. The data written into the frame memory 15 are read out from both the memory areas 15a and 15b in accordance with the television format. Under control of the timing signals outputted from the timing signal generator 27c the data read out are applied through the line buffer memory 27d to the D/A converter 27e where they are converted into an analog signal which may be applied as a video signal to the television monitor 28.

There will now be described the frame memory address generator 114 and the read/write mode selector 115 in the timing signal generator 27c by referring to FIG. 15. A control pulse of the control pulse generator 24, a raster address signal of the raster address generator 25, a basic pulse of the basic pulse generator 132, and further a display mode selection signal of the display mode selector 150 are supplied to the frame memory address generator 114. In addition to the control pulse and the basic pulse, the display mode selection signal is also supplied to the read/write mode selector 115. The display mode selection signal consists of a B-mode enable signal and a Doppler mode enable signal for respectively designating the memory areas 15a and 15b in accordance with the operation of a display mode selection switch 151 which is manually operated by an operator. Thus, it will be understood from the following that one of the display methods (i) and (ii) can be selected in response to the display mode selection signal.

The operation of the embodiment referred to with relation to FIGS. 11 and 12 will be described referring to FIGS. 13 and 15.

Figure 13A:
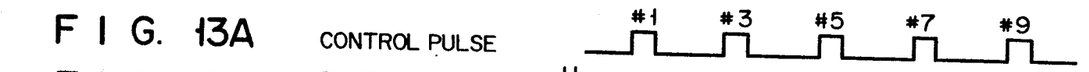
FIGS. 13 and 14 are timing charts for explaining the operation of the circuit shown in FIGS. 11 and 12.
Figures 13B, 13C, 13D:
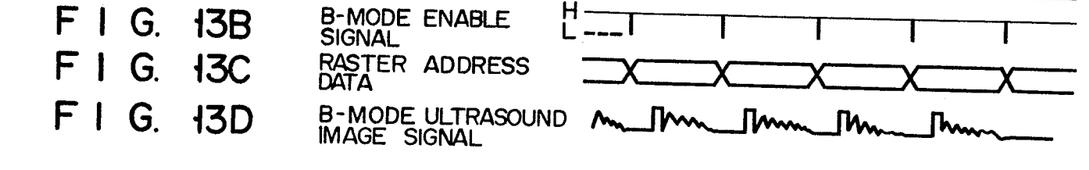

For the sake of the easy understanding, timing charts with respect to the B-mode ultrasound image and the Doppler data are separately explained in FIG. 13 and FIG. 14. However, it should be noted that the B-mode ultrasound image signal and the Doppler data signal are alternately supplied to the digital scan converter 27 at every control pulse. FIG. 13A is a signal waveform of the control pulse outputted from the control pulse generator 24. FIG. 13B is an output signal waveform of the display mode selector 150 (FIG. 15) which generates a mode select signal representing the B-mode enable signal when it is at high (H) level and the Doppler mode enable signal at low (L) level. FIG. 13C shows the raster address signal for designating the locations of the transmitting and receiving ultrasound waves by each control pulse. FIG. 13D shows a B-mode summed echo signal outputted from the amplifier/detector circuit 26. While the mode select signal in FIG. 13B is at H level, the B-mode data obtained are sequentially stored into the memory area 15a of the frame memory 15. The operation has been described already referring to FIG. 5 and no further description of it will be given here.

Figures 14A, 14B, 14C, 14D, 14E:
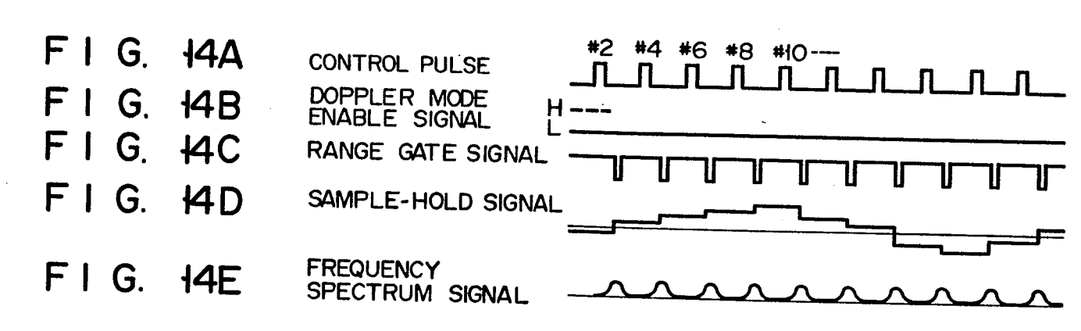

When the mode select signal is at L level as shown in FIG. 14B, the operation mode of the diagnosis apparatus is switched to the Doppler data store mode. At this time, the control pulse as shown in FIG. 14A is applied from its generator 24 to the Doppler pulser 41 (see FIG. 11). In accordance with the control pulse, the pulser 41 sends pulse signals to the probe 32 and the ultrasound beam DB for Doppler is transmitted to the object 12. The Doppler ultrasound echo reflected, for example, from the heart 14 in the object 12 is received by the Doppler probe 32 and is converted into an electric Doppler echo signal. The Doppler echo signal received and amplified by the amplifier 43 is phase-detected by the correlators 44 and 45. The phase detected signals from the correlators 44 and 45 are applied to low-pass filters 47 and 48 where only the low frequency component is derived. The signal filtered out is transferred to the sample-hold circuits 49 and 50. The range gate signal supplied from the range gate generator 46 has a timing set up corresponding to the location (a point MP in FIG. 10) where the Doppler deviation is to be detected, taking a waveform as shown in FIG. 14C. The sample-hold circuits 49 and 50 sample and hold the Doppler deviation signals and produce sample-held signals with the waveform as shown in FIG. 14D. The output signals from the sample-hold circuits 49 and 50 are subjected to the filtering process in the band-pass filters 51 and 52, and then are applied to the fast Fourier transform circuit 53. The fast Fourier transform circuit 53 transforms the Doppler deviation signals into a frequency distribution signal as shown in FIG. 14E which in turn is applied to the digital scan converter 27.

In the digital scan converter 27, the B-mode echo signal or the Doppler echo signal is alternately selected in accordance with the H and L levels of the mode select signal and is alternately applied to the A/D converter 27a. The output digital signal of the A/D converter 27a is loaded into the frame memory 15, through the line buffer memory 27b. The selection and conversion timings of the input signal in the A/D converter 27a, the operation timing of the line buffer memory 27b, the timings of the addressing and writing operation into the frame memory 15 are all controlled by the output signals of the timing signal generator 27c. In connection with the data writing into the frame memory 15, when the mode select signal is at H level, the B-mode image data are loaded into the memory area 15a while the Doppler data are loaded into the memory area 15b when the mode select signal is at L level.

The data loaded into the frame memory 15 are all read out repeatedly in the television format from the memory areas 15a and 15b at the intervals of time between the data write operations in substantially the same manner already described by referring to FIGS. 6A through 6D. The data read out are applied as an analog signal to the television monitor 28, via the line buffer memory 27d and the D/A converter 27e. Accordingly, on the screen of the monitor 28, the B-mode image and the Doppler data are concurrently displayed on the real time basis in accordance with the data stored in the memory 15 shown in FIG. 10. The mark signal from the marker circuit 54 is also applied to the analog digital converter of the digital scan converter 27. Accordingly, by being assigned the predetermined data to the addresses of the memory area 15a where the B-mode image data are stored, which correspond to given mark locations according to the mark signal, the data of the beam direction mark MB and the location mark MP may be loaded into the memory locations of the B-mode data and may be displayed on the screen of the monitor 28. It will be understood that the data of the marks MB and MP may be stored independently in a memory area allocated therefor.

What we claim is:

1. A compound mode ultrasound diagnosis apparatus comprising:
    transducer means for radiating ultrasound beams toward an object under examination and for receiving ultrasound echoes reflected therefrom;
    means for processing the ultrasound echoes so as to obtain B-mode ultrasound echo signals and M-mode ultrasound echo signals;
    digital scan converter means for converting the echo signals into video signals, said digital scan converter means including
    (a) analog-to-digital converter means for converting the echo signals into B-mode digital ultrasound echo data and M-mode digital ultrasound echo data,
    (b) memory means having first and second memory areas for storing said B-mode digital ultrasound echo data and said M-mode digital ultrasound echo data, respectively,
    (c) write control means for writing said B-mode digital ultrasound echo data and said M-mode digital ultrasound echo data into first and second memory areas, respectively,
    (d) read control means for reading out said B-mode digital ultrasound echo data and said M-mode digital ultrasound echo data and
    (e) digital-to-analog converter means for converting the B-mode and M-mode digital ultrasound echo data readout from said memory means into said video signals; and
    means for displaying the video signals.

2. A compound mode ultrasound diagnosis apparatus according to claim 1, wherein said transducer means includes means for producing control pulses, a pulser unit receiving said control pulses for producing ultrasound driving pulses delayed a predetermined time with respect to said control pulses, and a probe having a phased array ultrasound transducer for transmitting said ultrasound driving pulses and for receiving said ultrasound echoes;
    said processing means includes means for amplifying the ultrasound echoes received by said probe, means for delaying the amplified ultrasound echoes by predetermined time intervals, and means for combining said delayed ultrasound echoes to synthesize the B-mode ultrasound echo signals and the M-mode ultrasound echo signals;
    said memory means of said digital scan converter includes a first line buffer memory for making the digital data received from the analog-to-digital converter correspond to one ultrasound beam, and a frame memory for sequentially storing signals output from said first line buffer memory; and
    wherein said digital scan converter means further includes control means for generating timing signals delivered to said write and to said read control means to effect transfer of data to and from said frame memory.

3. A compound mode ultrasound diagnosis apparatus comprising:
    transducer means for radiating ultrasound beams toward an object under examination and for receiving ultrasound echoes reflected therefrom;
    means for processing the ultrasound echoes so as to obtain B-mode ultrasound echo signals and Doppler ultrasound echo signals;
    digital scan converter means for converting the echo signals into video signals, said digital scan converter means including
    (a) analog-to-digital converter means for converting the ultrasound echo signals into B-mode digital ultrasound echo data and Doppler digital ultrasound echo data,
    (b) memory means having first and second memory areas for storing said B-mode digital ultrasound echo data and said Doppler digital ultrasound echo data,
    (c) write control means for writing said B-mode digital ultrasound echo data and said Doppler digital ultrasound echo data into first and second memory areas, respectively,
    (d) read control means for reading out said B-mode digital ultrasound echo data and said Doppler digital ultrasound echo data in accordance with a television format, and
    (e) digital-to-analog converter means for converting the B-mode and Doppler digital ultrasound echo data read out from said memory means into said video signals; and
    means for displaying the video signals on a television screen.

4. A compound mode ultrasound diagnosis apparatus according to claim 3, wherein said transducer means includes means for producing control pulses, a pulser unit for producing ultrasound driving pulses having predetermined time delays with respect to said control pulses, a first probe having a phased array ultrasound transducer for transmitting said ultrasound driving pulses and for receiving ultrasound echoes corresponding thereto, a Doppler pulser for producing Doppler driving pulses in accordance with said control pulses, a Doppler probe for transmitting said Doppler driving pulses and for receiving Doppler echoes corresponding thereto, and means for supporting said Doppler probe;

said processing means includes an amplifier which amplifies the ultrasound echoes received by said first probe, means for delaying the amplified ultrasound echoes by predetermined time intervals, synthesizing means for synthesizing the delayed ultrasound echoes to form said B-mode ultrasound echo signals, a Doppler amplifier for amplifying the Doppler echoes received by said Doppler probe, means for forming phase detected signals from the amplified Doppler echoes, filter means for filtering the phase detected signals, means for sample-holding signals outputted from said filter means to produce Doppler deviation signals in accordance with a location for detecting Doppler deviation, and a fast Fourier transform circuit for converting the Doppler deviation signals into frequency distribution signals, whereby said B-mode ultrasound echo signals and said frequency distribution signals are written into said first and second memory areas of said memory means, respectively, by said digital scan converter means.

5. A compound mode ultrasound diagnosis apparatus according to claim 4, wherein said Doppler probe supporting means includes means for generating marker signals representative of a direction in which said Doppler pulses are transmitted from said Doppler probe and the Doppler detecting location, said marker signals being displayed together with the video signals corresponding to the B-mode digital ultrasound echo data.

6. A compound mode ultrasound diagnosis apparatus according to claim 4, wherein said digital scan converter means includes means for selectively converting said B-mode ultrasound echo signals and said Doppler echo signals into digital signals, a first line buffer memory for grouping the digital signals corresponding to one ultrasound beam, a frame memory for sequentially storing signals output from said first line buffer memory, means for converting data read out from said frame memory into an analog signal, and means for generating timing signals for controlling write and read operations of said frame memory.

7. A compound mode ultrasound diagnosis apparatus according to claim 4, wherein said supporting means has an archlike portion for producing a predetermined driving beam direction as said Doppler probe is moved along said supporting means.

8. A compound mode ultrasound diagnosis apparatus according to claim 3, wherein said transducer means includes means for producing control pulses, a pulser unit receiving said control pulses for producing ultrasound driving pulses delayed a predetermined time with respect to said control pulses, and a probe having a phased array ultrasound transducer for transmitting said ultrasound driving pulses and for receiving said ultrasound echoes;

said processing means includes means for amplifying the ultrasound echoes received by said probe, means for delaying the amplified ultrasound echoes by predetermined time intervals, and means for combining the delayed ultrasound echoes so as to synthesize the B-mode ultrasound echo signal and the Doppler ultrasound echo signals;

said memory means of said digital scan converter includes a first line buffer memory for making the digital data received from the analog-to-digital converter correspond to one ultrasound beam, and a frame memory for sequentially storing signals output from said first line buffer memory; and wherein said digital scan converter means further includes means for generating timing signals delivered to said write control means and to said read control means to effect transfer of data to and from said frame memory.

9. A compound mode ultrasound diagnosis apparatus comprising:

transducer means for radiating ultrasound beams toward an object under examination and for receiving ultrasound echoes reflected therefrom;

means for processing the ultrasound echoes to obtain ultrasound echo signals corresponding to distinct scan modes;

digital scan converter means for converting the echo signals into video signals, said digital scan converter means including (a) analog-to-digital converter means for converting said ultrasound echo signals into at least two distinct sets of digital ultrasound echo data, each set of said digital data corresponding to a different one of said distinct scan modes, (b) memory means having a plurality of distinct memory areas for storing said at least two sets of digital ultrasound echo data, (c) write control means for respectively writing said at least two sets of digital ultrasound data into said memory means, each set of said digital data being stored together in a distinct memory area, (d) read control means for reading out said at least two sets of digital ultrasound data in accordance with a television format, (e) digital-to-analog converter means for converting the digital ultrasound data read out from said memory means into video signals; and means for displaying the video signals on a television screen, so as to form noninterlaced separate images corresponding to said distinct scan modes.

10. A compound mode ultrasound diagnosis apparatus according to claim 9, wherein said transducer means includes means for producing control pulses, a pulser unit for receiving said control pulses and for producing ultrasound driving pulses delayed a predetermined time with respect to said control pulses, and a probe having a phased array ultrasound transducer for transmitting said ultrasound driving pulses and for receiving said ultra sound echoes;

said processing means includes means for amplifying the ultrasound echoes received by said probe, means for delaying the amplified ultrasound echoes by predetermined time intervals, and means for combining the delayed ultrasound echoes so as to synthesize said ultrasound echo signals corresponding to said distinct scan modes;

said memory means of said digital scan converter including a first line buffer memory for making the digital data received from the analog-to-digital converter means correspond to one ultrasound beam, and a frame memory for sequentially storing signals output from said first line buffer memory; and wherein said digital scan converter means further includes means for generating timing signals delivered to the write control means and to the read control means to effect transfer of data to and from said frame memory.

* * * * *